United States Patent [19]
Carpenter et al.

[11] Patent Number: 5,425,768
[45] Date of Patent: Jun. 20, 1995

[54] REINFORCED SPACER FOR STEM-TYPE PROSTHETIC IMPLANTS

[76] Inventors: Charles W. Carpenter, 332 Bunn Hill Rd., Vestal, N.Y. 13850; Rafail Zubok, 222 Spruce St., Midland Park, N.J. 07432

[21] Appl. No.: 27,517

[22] Filed: Mar. 8, 1993

[51] Int. Cl.⁶ ............................................. A61F 2/38
[52] U.S. Cl. ............................................. 623/6; 623/23
[58] Field of Search .................... 623/16, 18, 19, 20, 623/23

[56] References Cited

U.S. PATENT DOCUMENTS

| | | | |
|---|---|---|---|
| 3,589,011 | 6/1971 | Sneer | 433/174 |
| 3,717,932 | 2/1973 | Brainin | 433/175 |
| 4,195,409 | 4/1980 | Child | 433/175 |
| 4,670,015 | 6/1987 | Freeman | 623/23 |
| 4,888,023 | 12/1989 | Averill et al. | 623/23 |
| 4,904,267 | 2/2990 | Bruce et al. | 623/23 |
| 5,030,234 | 7/1991 | Pappas et al. | 623/23 |
| 5,035,712 | 7/1991 | Hoffman | 623/23 |
| 5,041,141 | 8/1991 | Ypma et al. | 623/23 |
| 5,047,035 | 9/1991 | Mikhail et al. | 623/23 |
| 5,057,101 | 10/1991 | Dorr et al. | 623/23 |
| 5,061,287 | 10/1991 | Feiler | 623/23 |
| 5,062,854 | 11/1991 | Noble et al. | 623/23 |
| 5,078,746 | 1/1992 | Garner | 606/95 |
| 5,080,679 | 1/1992 | Pratt et al. | 623/23 |
| 5,080,680 | 1/1992 | Mikhail et al. | 623/23 |
| 5,092,892 | 3/1992 | Ashby | 606/95 |
| 5,108,437 | 4/1992 | Kenna | 603/23 |
| 5,169,400 | 12/1992 | Muhling et al. | 606/72 |

*Primary Examiner*—David Isabella
*Attorney, Agent, or Firm*—Samuelson & Jacob

[57] ABSTRACT

A spacer for use in the centering of the far end portion of the stem of a prosthetic implant is molded of a synthetic polymeric material compatible with the cement employed to affix the prosthetic implant within the natural bone and includes a post for coupling the spacer with the stem, a flanged spacer portion for extending longitudinally and radially beyond the stem to engage the natural bone for centering the stem, and a reinforcing core extending longitudinally into the post and into the flanged spacer portion to reinforce the spacer against stresses to which the spacer is subjected, especially at a location between the post and the flanged spacer portion of the spacer, during implant and during subsequent curing of the cement.

20 Claims, 2 Drawing Sheets

REINFORCED SPACER FOR STEM-TYPE PROSTHETIC IMPLANTS

The present invention relates generally to prosthetic implants and pertains, more specifically, to stem-type prostheses such as a femoral prosthesis to be affixed within the femur for providing a replacement ball at the proximal femur.

It is conventional, in the implant of a femoral prosthesis, to insert the stem of the prosthesis longitudinally into a passage in the prepared femur and to affix the stem, at least along a portion of the length of the stem, within the passage through the use of cement. In this manner, the stem is coupled directly to the natural bone of the femur. The outside diameter of the stem is made smaller than the inside diameter of the passage so as to provide a space for the cement and to facilitate insertion of the stem during implant. In order to facilitate insertion and maintain the stem essentially centered within the passage, both during insertion and while the cement cures, a centering device, or spacer, is provided at the distal end of the stem to guide and maintain the distal end of the stem essentially centered in the passage.

It is desirable that the spacer be constructed of a material compatible with the cement. The most commonly used cement is a methyl methacrylate, commonly referred to as PMMA, and the spacer advantageously is molded of methyl methacrylate (PMMA) so that after insertion of the stem and upon curing of the cement, the material of the cement and the material of the spacer are joined in an integral cement mantle, with the spacer preferably becoming essentially indistinguishable from the surrounding cement. However, spacers molded of PMMA tend to be somewhat brittle and therefore subject to fracture during implant and subsequent curing of the cement in the passage. Fracture of the spacer during insertion or during curing of the cement could lead to a shift in the stem relative to the surrounding bone, generally to either a varus or a valgus position, resulting in an incongruent cement mantle having relatively thin, weakened portions, leading to potential loosening of the stem during service.

The present invention provides an improved spacer which resists the above-described shift in the position of the stem of a stem-type prosthetic implant and which attains several objects and advantages, some of which are summarized as follows: Enables the use of a spacer constructed of a material compatible with the cement employed in the cemented affixation of a stem-type prosthesis within the natural bone of a recipient, which spacer will maintain guiding and centering functions during insertion of the stem into a passage in the prepared natural bone, during any impaction of the prosthesis, and during subsequent curing of the cement in the passage; provides a spacer for use in connection with any selected one of a plurality of stem-type prosthetic implants having stems of different sizes; provides a reinforced construction in a spacer for resisting fracturing stresses encountered during insertion, during any impaction, and during curing of the cement in a cemented implant procedure; enables the spacer to function properly even where excessive stresses may actually fracture particularly vulnerable portions of the spacer; promotes ease of implant and a better fit by facilitating the choice of a spacer of appropriate dimensions for coupling with a selected stem size; provides a radiographic marker in a spacer constructed of an essentially radio-transparent synthetic polymeric material; provides a wider range of choices in the design and configuration of stem-type prosthetic implants; promotes superior performance in stem-type prosthetic implants over an extended service life.

The above objects and advantages, as well as further objects and advantages, are attained by the present invention which may described briefly as a spacer for use in connection with a stem-type prosthetic implant in which the prosthetic implant includes a stem extending longitudinally between a near end and a far end for insertion into a passage in the natural bone within which the prosthetic implant is to be implanted, a far end portion adjacent the far end, and a bore extending longitudinally into the far end portion toward the near end, the far end portion having a predetermined overall diameter, the spacer comprising: a spacer portion constructed of a synthetic polymeric material and including spacer elements arrayed circumferentially around the spacer portion; a post integral with the spacer portion, the post extending longitudinally from the spacer portion and having an outer surface; and a reinforcing core embedded within the spacer portion and extending longitudinally so as to be integral with the post; the relative dimensions and location of the outer surface of the post and the bore in the far end of the stem, and the relative dimensions and location of the spacer elements and the far end portion of the stem being such that the post is receivable within the bore for affixing the spacer to the far end portion with the spacer elements extending longitudinally beyond the far end portion and laterally beyond the predetermined diameter of the far end portion of the stem for engaging the natural bone, upon insertion of the stem during implant, to essentially center the far end portion of the stem within the passage.

The invention will be understood more fully, while still further objects and advantages will become apparent, in the following detailed description of a preferred embodiment of the invention illustrated in the accompanying drawing, in which.

Figures 1, 2:
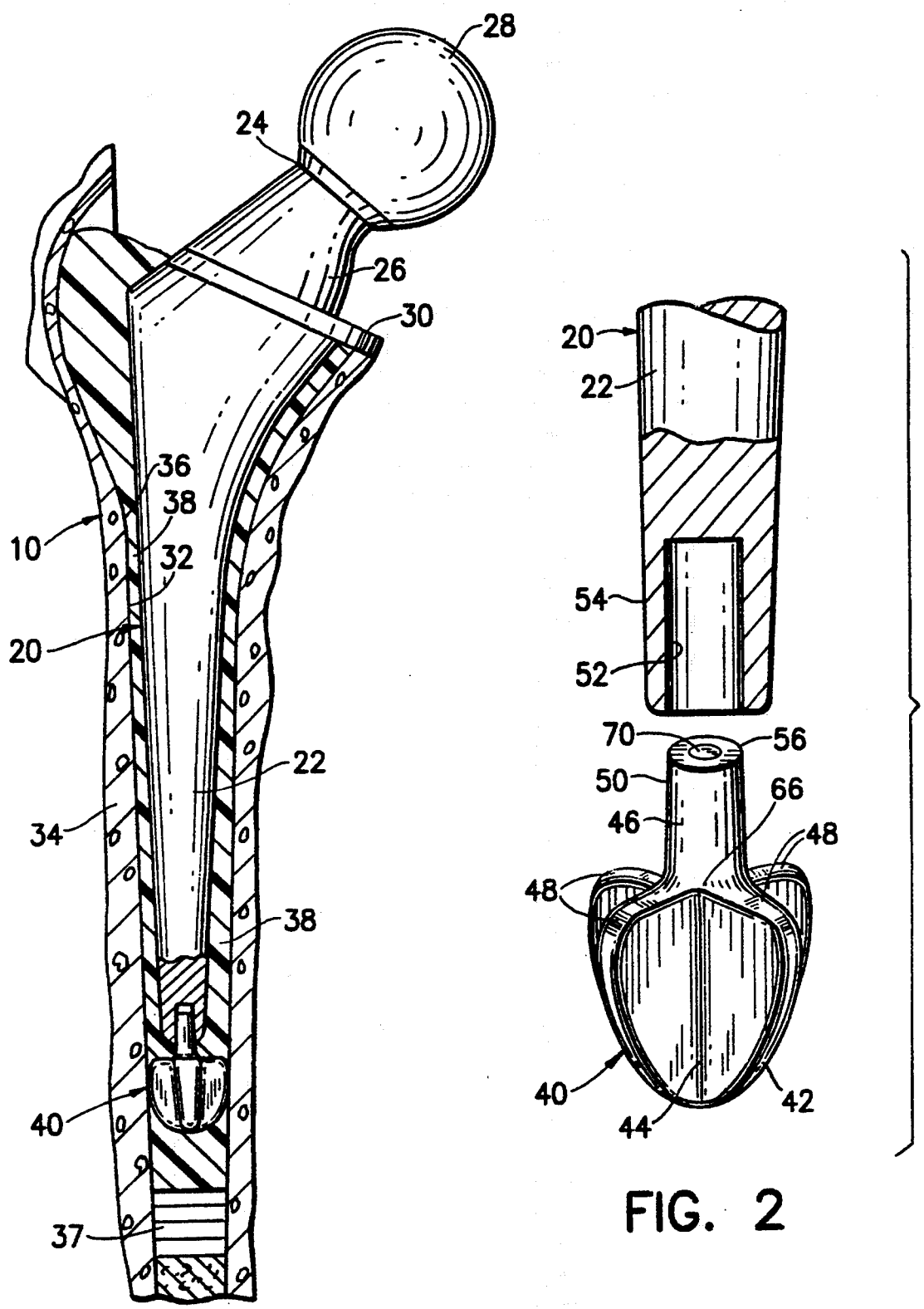
FIG. 1 is a longitudinal cross-sectional view showing a stem-type prosthesis implanted within a femur, the prosthetic implant including a spacer constructed in accordance with the present invention.
FIG. 2 is an enlarged, partially sectioned pictorial view showing the spacer being applied to the distal end portion of the prosthesis, prior to implant.

Referring now to the drawing, and especially to FIG. 1 thereof, the proximal end of a femur 10 has been resected for the implant of a femoral prosthesis. A femoral prosthesis is illustrated at 20 and is shown implanted at the prepared proximal end of the femur 10. Femoral prosthesis 20 is of the type having a stem 22 which is inserted into the prepared proximal portion of the femur 10 to be affixed to the femur 10 so that a prosthetic portion 24 which is unitary with the stem 22 at the near or proximal end of the stem 22 of the prosthesis will provide a neck 26 upon which is placed a spherical head 28 for engagement with either the natural acetabulum or an acetabular prosthesis for articulation in a hip replacement. The femur 10 is prepared to receive prosthesis 20 by cutting to establish a neck resection level at 30 and then creating a passage 32 within the wall 34 of the femur 10 as a part of a cavity 36 in the prepared femur 10 for receiving the stem 22 of the prosthesis 20. A conventional bone plug 37 is inserted, as shown. Cement 38 is placed in the cavity 36 and the far or distal end of the stem 22 is inserted into passage 32 and advanced longitudinally downwardly, through the uncured cement 38, until the stem 22 is seated fully within the passage 32. Alternately, cement 38 may be injected into cavity 36 subsequent to insertion of the stem 22. Upon proper seating of the prosthesis 20 in the cavity 36 of the prepared femur 10, as shown, a mantle of cement 38 surrounds the stem 22 and, upon curing of the cement 38, affixes the stem 22 to the corresponding proximal portion of the femur 10. In order to assure proper affixation by the mantle of cement 38, the passage 32 is larger in diameter than the predetermined diameter of the stem 22, and the stem 22 essentially is centered within the passage 32 of cavity 36 to establish an appropriate congruent mantle of cement 38 about the stem 22, the mantle of cement 38 having at least a minimum thickness throughout for providing the strength necessary for proper affixation. To that end, a spacer, shown in the form of distal spacer 40, constructed in accordance with the present invention, is placed at the far or distal end of the stem 22.

Turning now to FIG. 2, distal spacer 40 is seen to include a spacer member in the form of a spacer portion 42 having a main body in the form of a hub 44, and a post 46 extending longitudinally from the spacer portion 42. A plurality of spacer elements in the form of flanges 48 extend laterally from the hub 44. The post 46 has an outer surface 50 generally complementary with a bore 52 which extends longitudinally into a far or distal end portion 54 located at the far or distal end of the stem 22 of prosthesis 20, the bore 52 extending from the distal end of the stem 22 toward the proximal end of the prosthesis 20. Distal spacer 40 is coupled to the stem 22 by insertion of the post 46 into the bore 52, the relative dimensions of the post 46 and the bore 52 being such that the distal spacer 40 is affixed properly in the distal end portion 54 of the stem 22. Outer surface 50 of the post 46 is generally frusto-conical and is tapered from a larger diameter adjacent the spacer portion 42 to a smaller diameter at the upper end 56 of the post 46, which upper end 56 is spaced longitudinally away from the spacer portion 42. The tapered configuration assures an appropriate connection between the distal spacer 40 and the stem 22 upon seating of the post 46 within the bore 52. Once the distal spacer 40 is coupled with the stem 22, the spacer portion 42 is located longitudinally beyond the far or distal end of the stem 22 and the flanges 48 extend laterally beyond the predetermined diameter of the stem 22 to engage the natural bone of the femur 10 for centering purposes.

Figure 3:
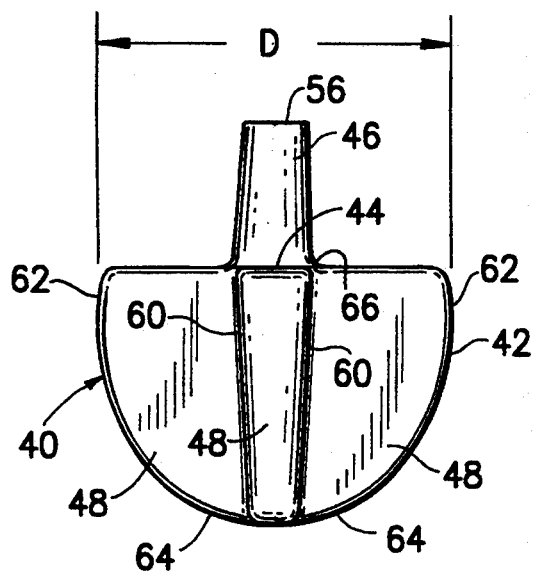
FIG. 3 is an elevational view of the spacer.
Figure 4:
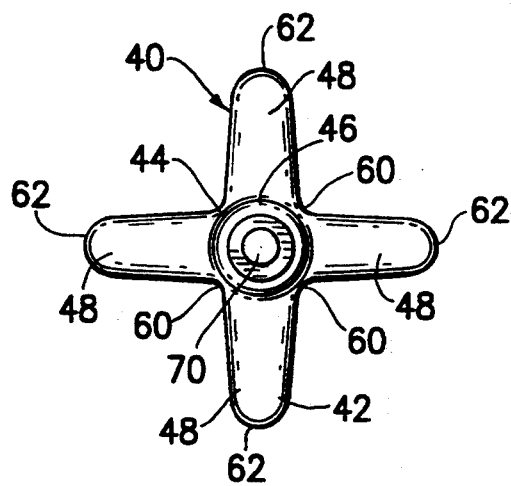
FIG. 4 is a top plan view of the spacer.
Figure 5:
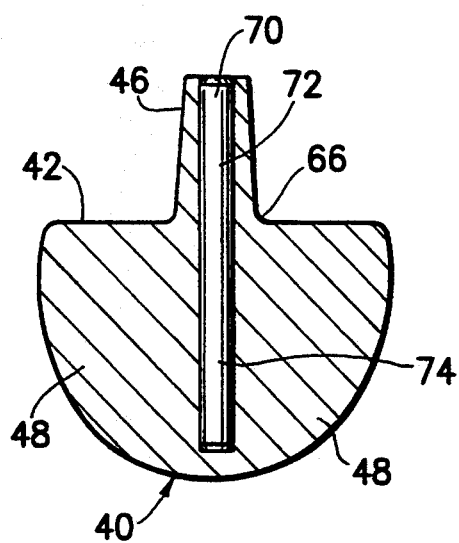
FIG. 5 is a longitudinal cross-sectional view of the spacer.

Turning now to FIGS. 3 through 5, as well as to FIGS. 1 and 2, distal spacer 40 preferably includes four flanges 48 spaced equidistantly circumferentially around the hub 44 so as to be arrayed orthogonally about the hub 44. Each flange 48 extends radially outwardly from a root 60 at the hub 44 to a crest 62 at an overall diameter D, and has a rounded leading edge 64. The rounded leading edges 64 facilitate insertion of the stem 22 into passage 32 during implant, and the crests 62 are radially equidistant from the hub 44 so as to engage the bone of the femur 10 to center the stem 22 within the passage 32. The circumferential spacing between the flanges 48 enables the uncured cement 38 to pass the distal spacer 40, as the stem 22 is being inserted during implant, or as cement is injected after insertion of the stem 22.

The employment of the post 46 and bore 52 connection at the distal end portion 54 of the stem 22 of prosthesis 20 enables the provision of distal spacers 40 of differing dimensions for connection to stems 22 of various diameters so as to allow a surgeon to select any combination of stem 22 and distal spacer 40 to accommodate the requirements of a particular recipient of prosthesis 20. Thus, a plurality of distal spacers 40 having flanges 48 of different radial extent for providing a range of overall diameters D all include a post 46 of single standard dimensions to cooperatively engage a bore 52 of single complementary dimensions placed in each of a number of different stems 22 so as to enable the selection of a particular size distal spacer 40 for attachment to a particular prosthesis 20 to attain the fit required in a particular recipient.

Distal spacer 40 is constructed of a synthetic polymeric material compatible with cement 38. Since the preferred cement is a methyl methacrylate, commonly referred to as PMMA, the distal spacer 40 preferably is molded of PMMA. Thus, upon curing of the cement 38, subsequent to insertion of the stem 22 fully into the passage 32, a chemical bond is created between the cement 38 and the distal spacer 40 so that the distal spacer 40 becomes essentially indistinguishable from the mantle of cement 38 insofar as the mechanical characteristics of the connection between the stem 22 and the bone of the femur 10 are concerned. However, PMMA is a relatively brittle material and is susceptible to fracture if subjected to excessive stress during insertion of the stem 22 into the passage 32 and impaction of the prosthesis 20. The material of the distal spacer 40 may be made even more brittle by the practice of impregnating the PMMA with barium for the purpose of rendering the material somewhat radio-opaque. More particularly, stresses at a vulnerable location 66, where the post 46 meets the flanged spacer portion 42 of the distal spacer 40, can become concentrated to the point where a fracture can occur between the post 46 and the spacer portion 42. Such a fracture could allow the distal end portion 54 of the stem 22 to become skewed within the passage 32, thereby causing undesirable incongruity in the mantle of cement 38. In order to preclude such an occurrence, distal spacer 40 is provided with a reinforcing core, shown in the form of a rod 70, embedded within the hub 44 and extending longitudinally into the post 46 and into the spacer portion 42, in lateral juxtaposition with the flanges 48, adjacent the root 60 of each flange 48. Rod 70 preferably is constructed of a biocompatible metal alloy, such as a cobalt chrome alloy, and reinforces the distal spacer 40 adjacent the intersection of the post 46 and the spacer portion 42, so as to resist fracture of the distal spacer 40, especially at the vulnerable location 66. Moreover, rod 70 preferably is secured within the hub 44 at 72, along the post 46, and at 74, within the spacer portion 42 laterally adjacent the roots 60 of the flanges 48, as by a tight fit between the rod 70 and the hub 44, so that even if a fracture should occur at 66, the flanged spacer portion 42 of the distal spacer 40 will not be separated from the post 46, and the distal spacer 40 still will function to maintain the distal end portion 54 of the stem 22 centered within the passage 32 during insertion of the stem 22 into the passage 32. Rod 70 may be embedded within hub 44 of distal spacer 40 in several different ways; however, the preferred methods are either by molding the hub 44, with post 46 and spacer portion 42, around the rod 70, or by providing the hub 44 with a central hole 76 and then inserting the rod 70 into the hole 76 subsequent to molding.

The employment of metal alloy rod 70 provides a radiographic function so that conventional barium impregnation need not be employed to enable radiographic detection of the position of the distal spacer 40.

It will be seen that the spacer 40 attains the several objects and advantages summarized above, namely: Enables the use of a spacer constructed of a material compatible with the cement employed in the cemented affixation of a stem-type prosthesis within the natural bone of a recipient, which spacer will maintain guiding and centering functions during insertion of the stem into a passage in the prepared natural bone, during any impaction of the prosthesis, and during subsequent curing of the cement in the passage; provides a spacer for use in connection with any selected one of a plurality of stem-type prosthetic implants having stems of different sizes; provides a reinforced construction in a spacer for resisting fracturing stresses encountered during insertion, during any impaction, and during curing of the cement in a cemented implant procedure; enables the spacer to function properly even where excessive stresses may actually fracture particularly vulnerable portions of the spacer; promotes ease of implant and a better fit by facilitating the choice of a spacer of appropriate dimensions for coupling with a selected stem size; provides a radiographic marker in a spacer constructed of an essentially radio-transparent synthetic polymeric material; provides a wider range of choices in the design and configuration of stem-type prosthetic implants; promotes superior performance in stem-type prosthetic implants over an extended service life.

It is to be understood that the above detailed description of an illustrated preferred embodiment of the invention is provided by way of example only. Various details of design and construction may be modified without departing from the true spirit and scope of the invention, as set forth in the appended claims.

The embodiments of the invention in which an exclusive property or privilege is claimed are defined as follows:

1. A spacer for use in connection with a prosthetic implant having a stem extending longitudinally between a proximal end and a distal end for insertion into a passage in the natural bone within which the prosthetic implant is to be implanted, a distal end portion adjacent the distal end, and a bore extending longitudinally into the distal end portion toward the proximal end, the distal end portion having a predetermined diameter, the spacer comprising:
   a spacer member constructed of a synthetic polymeric material and including a main body and spacer elements arrayed circumferentially around the spacer member and extending laterally from the main body to an overall diameter;
   a post integral with the spacer member, the post extending longitudinally from the spacer member and having an outer surface with a diameter smaller than the overall diameter of the spacer member; and
   a reinforcing core embedded within the spacer member and extending longitudinally so as to be integral with the post;
   the post being receivable within the bore of the stem for affixing the spacer to the distal end portion with the spacer elements extending longitudinally beyond the distal end portion and laterally beyond the predetermined diameter of the distal end portion of the stem for engaging the natural bone, upon insertion of the stem during implant, to essentially center the distal end portion of the stem within the passage.

2. The invention of claim 1 wherein the synthetic polymeric material of the spacer member is selected from materials compatible with cement utilized to secure the prosthetic implant within the natural bone.

3. The invention of claim 2 wherein the spacer member is molded of PMMA.

4. The invention of claim 2 wherein the reinforcing core comprises a rod constructed of a biocompatible metal alloy.

5. The invention of claim 4 wherein the spacer member and the post are molded of PMMA in a unitary construction.

6. The invention of claim 5 wherein the reinforcing rod extends into the post and is secured to the spacer member within the spacer portion and to the post within the post.

7. The invention of claim 6 wherein the outer surface of the post is frusto-conical and is tapered from a larger diameter adjacent the spacer member toward a smaller diameter spaced longitudinally proximal from the spacer member.

8. A spacer for use in connection with a prosthetic implant having a stem extending longitudinally between a proximal end and a distal end for insertion into a passage in the natural bone within which the prosthetic implant is to be implanted, a distal end portion adjacent the distal end, and a bore extending longitudinally into the distal end portion toward the proximal end, the distal end portion having a predetermined diameter, the spacer comprising:
   a hub;
   a spacer member integral with the hub, the spacer member including spacer elements arrayed circumferentially around the hub and extending laterally from the hub, each spacer element including a root at the hub and a crest spaced laterally from the root to an overall diameter;
   a post integral with the hub, the post extending longitudinally from the spacer member and having an outer surface with a diameter smaller than the overall diameter of the spacer member;
   the hub, the post and the spacer member being constructed of a synthetic polymeric material; and
   a reinforcing core embedded within the hub and extending longitudinally so as to extend into the post and into the spacer member to be laterally juxtaposed with the spacer elements adjacent the roots of the spacer elements;
   the post being receivable within the bore of the stem for affixing the spacer to the distal end portion with the spacer elements extending longitudinally beyond the distal end of the stem and laterally beyond the predetermined diameter of the distal end portion of the stem for engaging the natural bone, upon insertion of the stem during implant, to essentially center the distal end portion of the stem within the passage.

9. The invention of claim 8 wherein the reinforcing core comprises a rod, and the rod is secured to the hub at the post and at the spacer member.

10. The invention of claim 8 wherein the synthetic polymeric material of the hub, the spacer member and the post is selected from materials compatible with cement utilized to secure the prosthetic implant within the natural bone.

11. The invention of claim 10 wherein the spacer member and the post are molded of PMMA in a unitary construction.

12. The invention of claim 11 wherein the reinforcing core comprises a rod constructed of a biocompatible metal alloy.

13. The invention of claim 12 wherein the rod is secured to the hub at the post and at the spacer member.

14. The invention of claim 8 wherein the spacer elements each comprise a flange extending from the hub, in a radial direction from a corresponding root to a corresponding crest.

15. The invention of claim 14 wherein the reinforcing core comprises a rod, and the rod is secured to the hub at the post and at the spacer member.

16. The invention of claim 14 wherein the synthetic polymeric material of the hub, the spacer member and the post is selected from materials compatible with cement utilized to secure the prosthetic implant within the natural bone.

17. The invention of claim 16 wherein the spacer member and the post are molded of PMMA in a unitary construction.

18. The invention of claim 17 wherein the reinforcing core comprises a rod constructed of a biocompatible metal alloy.

19. The invention of claim 18 wherein the rod is secured to the hub at the post and at the spacer member.

20. The invention of claim 19 including four flanges arrayed orthogonally about the hub.

* * * * *